US007935850B2

(12) United States Patent
Caers et al.

(10) Patent No.: US 7,935,850 B2
(45) Date of Patent: May 3, 2011

(54) PROCESS FOR HYDROFORMYLATION OF PROPYLENE

(75) Inventors: Raphael Frans Caers, Edegem (BE); Eddy Theophyle Andrea Van Driessche, Eeklo (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 933 days.

(21) Appl. No.: 10/591,733

(22) PCT Filed: Jan. 28, 2005

(86) PCT No.: PCT/EP2005/000948
§ 371 (c)(1),
(2), (4) Date: Jun. 6, 2007

(87) PCT Pub. No.: WO2005/095315
PCT Pub. Date: Oct. 13, 2005

(65) Prior Publication Data
US 2007/0282134 A1    Dec. 6, 2007

(51) Int. Cl.
*C07C 45/50* (2006.01)
(52) U.S. Cl. .................. 568/451; 568/452; 568/454
(58) Field of Classification Search .......... 568/451, 568/452, 454
See application file for complete search history.

(56) References Cited

U.S. PATENT DOCUMENTS

| 4,247,486 A | 1/1981 | Brewester et al. | 568/454 |
| 4,593,127 A | 6/1986 | Bunning et al. | 568/454 |
| 4,760,194 A | 7/1988 | Phillips et al. | 568/454 |
| 5,960,643 A | 10/1999 | Kuechler et al. | 62/620 |
| 6,583,324 B2 * | 6/2003 | Takai et al. | 568/451 |
| 2002/0103406 A1 | 8/2002 | Mathys et al. | 585/329 |

FOREIGN PATENT DOCUMENTS

| DE | 100 35 370 | 3/2001 |
| GB | 1 387 657 | 3/1975 |

OTHER PUBLICATIONS

Beller et al., entitled "Progress in Hydroformylation and Carbonylation" Journal of Molecular Catalysis A: Chemical., vol. 104, 1995, pp. 17-85, Germany.

\* cited by examiner

*Primary Examiner* — James O Wilson
*Assistant Examiner* — Ebenezer Sackey
(74) *Attorney, Agent, or Firm* — Andrew B. Griffis; Leandro Arechederra, III

(57) ABSTRACT

Increasing the propylene content of the propylene feed delivered to a continuous hydroformylation process from the 95 mole % maximum level that is usual in typical chemical grade propylene to at least 97 mole %, for example to the 97.5% level obtainable from the conversion of oxygenates to olefins or the 99.5% level of polymer grade propylene, enables adjustments to be made in the syngas feed to the process. This leads to surprising improvements in hydroformylation product yield, in reactor capacity utilization and in the reduction of amounts of waste gases.

44 Claims, 4 Drawing Sheets

PROCESS FOR HYDROFORMYLATION OF PROPYLENE

CROSS REFERENCE TO RELATED PATENT APPLICATIONS

This application is a national stage filing of International Patent Cooperation Treaty Application No. PCT/EP2005/000948 filed Jan. 28, 2005, which claims priority from U.S. Ser. No. 10/805,983 filed Mar. 22, 2004, the disclosure of which is fully incorporated herein by reference.

FIELD OF THE INVENTION

The present invention relates to improvements in or relating to the commercial scale hydroformylation of propylene to produce butyraldehyde and butanol.

BACKGROUND OF THE INVENTION

Processes for the hydroformylation of propylene to produce butyraldehyde and butanol are well known and are practised widely. They typically employ liganded rhodium catalysed low pressure hydroformylation technology, sometimes known as the low pressure oxo (LPO) process, in which propylene is reacted with a mixture of carbon monoxide and hydrogen (known as syngas). Examples of the commercial operation of such a process are given in U.S. Pat. No. 4,247,486 and in GB-A-1,387,657.

For economic reasons, the raw material used for such industrial scale processes has been chemical grade propylene, which contains about 90-95 wt % propylene, with the majority of the balance being propane. Industrial hydroformylation processes are generally continuous processes which do not result in 100% conversation of the propylene. The selectivity to desired products is also not 100%, and a small portion of the propylene is hydrogenated to propane. Accordingly, the products of the hydroformylation of chemical grade propylene include the target butyraldehyde and butanol streams and an off gas stream containing unreacted propylene, propane and unreacted carbon monoxide and hydrogen.

It is of course economically desirable that the unreacted propylene, carbon monoxide and hydrogen be recycled. However, in order for the continuous hydroformylation process to operate successfully on an industrial scale, it is important to establish a steady state between the feed materials, including any recycle, and the degree of reaction. It is therefore important to prevent excessive propane build up in the reaction system due to the recycle of the unreacted components. However, propane and propylene are difficult to separate and thus, in order to prevent propane build up due to the recycle, it is necessary to vent off some, if not all, of the propane. This removal of propane however also involves the removal of some propylene resulting in some inefficiencies and economic debits in the process.

The present invention is concerned with the conditions that enable benefits to be realised from the use of propylene feeds of higher purity. In particular the invention is concerned with the conditions that enable benefits to be realised from the use of a propylene feedstock containing at least 97 mole % propylene, especially a propylene feedstock known as polymer grade propylene. DE-A-10035370 is concerned with an improved two reactor recycle hydroformylation system which reduces propylene losses. This recycle system is said to reduce propylene loss in the off gas. In the Example, polymer grade propylene which contains about 99.5 wt % propylene, the 0.5 wt % balance being propane, is used as the feedstock for low pressure, rhodium catalysed, hydroformylation.

The production of hydroformylated products from an olefin stream made by thermal or catalytic cracking or by dehydrogenation processes can be negatively impacted as a result of undesirable by-products coming into contact with hydroformylation catalysts. Such by-products can cause reduced efficiency in the recovery of useful hydroformylation products or can cause the formation of lower quality derivative products.

Removal of undesirable by-products from an olefin stream can be quite difficult. For example the removal of sulphur, nitrogen and chlorine from cracked hydrocarbon streams, or the removal of dimethyl ether (DME) from C4 or C5 raffinate recovered from a methyl tertiary butyl ether (MTBE) or a tertiary amyl methyl ether (TAME) unit, can require a significant amount of olefin feed pretreatment. It is, therefore, also desirable to find methods of hydroformylating olefin compositions which do not require extensive pretreatment of the olefin feed to remove contaminants.

SUMMARY OF THE INVENTION

According to the present invention there is provided a continuous process for the hydroformylation of propylene comprising feeding (i) a propylene stream at a rate of at least 3 tonnes per hour, and (ii) synthesis gas comprising hydrogen and carbon monoxide, to a hydroformylation reactor in which the propylene is hydroformylated over a rhodium containing catalyst, characterised in that (a) the propylene stream contains at least 97 mole % of propylene; (b) the molar ratio of $(H_2+CO)$ contained in the fresh synthesis gas fed to the process, to the propylene contained in the fresh propylene stream fed to the process, is greater than 1.93; and (c) in the synthesis gas feed, the hydrogen is present in molar excess over the amount of carbon monoxide.

By "tonnes" is meant metric tonnes, so 3 tonnes per hour is 3000 kg per hour—in other words, an industrial scale process. Of course, the feed rate is that applicable during normal operation of the process. Shut down of the process for maintenance and other reasons may occur without impacting the scope of the invention.

The term synthesis gas is sometimes abbreviated herein, in accordance with conventional practice, to syngas. Syngas primarily comprises hydrogen and carbon monoxide, but it may contain a few mole % of other components such as methane and/or carbon dioxide.

DETAILED DESCRIPTION OF THE INVENTION

Figure 1:
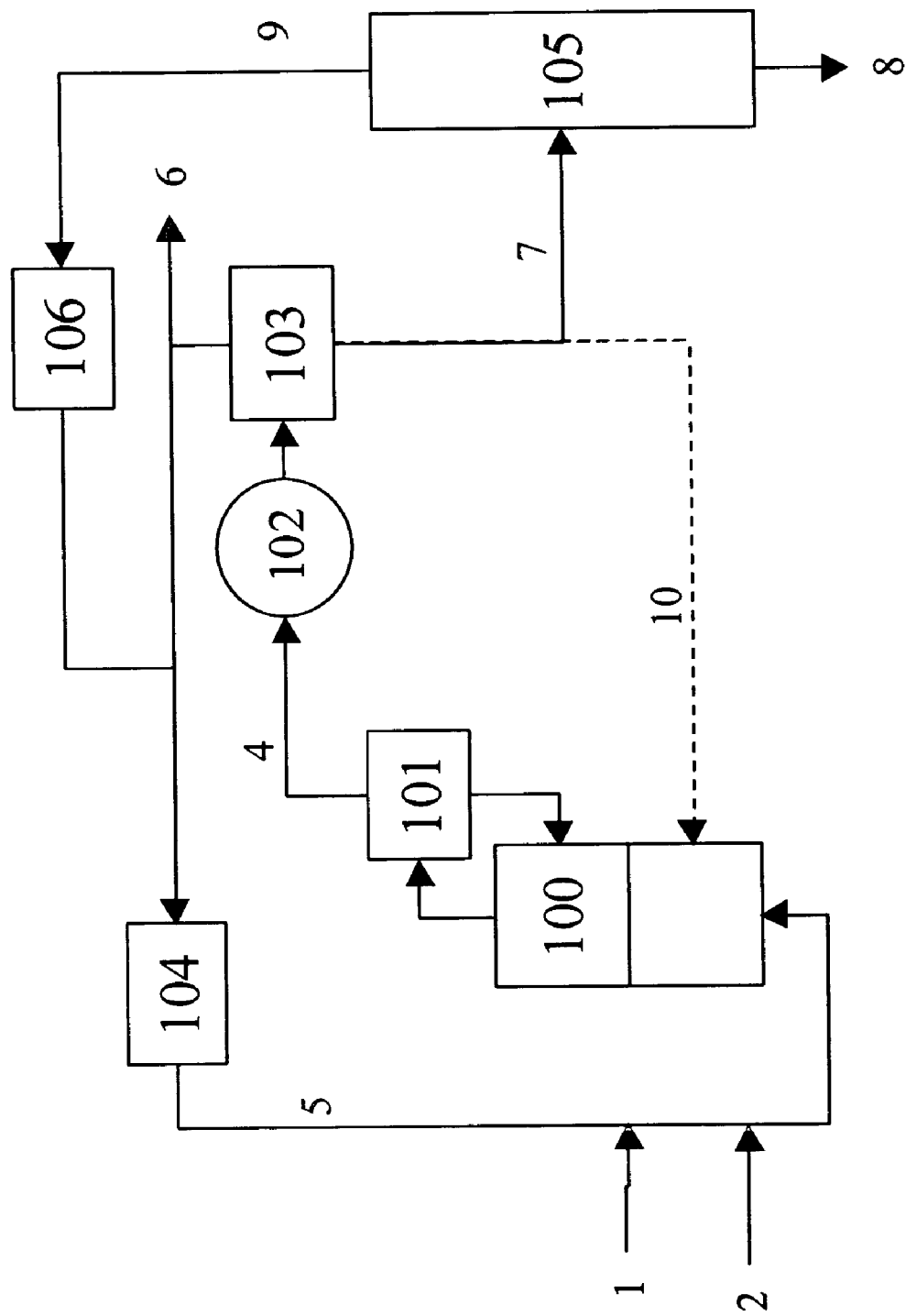
FIG. 1 shows a simplified flow scheme of a low pressure rhodium hydroformylation process useful for performance of the invention. It is further described in Example 1.

The ratio of $(H_2+CO)$/propylene as specified above relates to fresh reaction components introduced into the process. The actual ratio of such components present in the hydroformylation reactor may be different due to the concentration-changing effects of recycle and of gas venting from the system. Preferably the said ratio is greater than 1.935, more preferably greater than 1.94. The preferred maximum value for the ratio is 2.10, with progressively preferred maxima being, in order, 2.05, 2.00, 1.98, 1.97, 1.96 and 1.95. Ranges for said ratio between any of the stated minimum or preferred minimum values and any of the stated preferred maximum values are, therefore, countenanced for use in performance of the invention.

Hydroformylation is desirably carried out at a temperature of from about 40 to about 200° C., more desirably from about 80 to about 180° C., and preferably from about 90 to about 155° C.

The reaction is also desirably carried out at a low pressure, e.g., a pressure of about 0.05 to about 10 MPa (absolute), preferably about 0.1 to about 6 MPaa, more preferably below 5 MPaa, yet more preferably below 3.5 MPaa, and most preferably below about 2.5 MPaa. It is particularly preferred that the carbon monoxide partial pressure be not greater than about 50% of the total pressure. The proportions of carbon monoxide and hydrogen present in the fresh syngas used in the hydroformylation (also known as oxo) reactor that is operating at the foregoing pressures are desirably maintained as follows: CO from about 1 to about 50 mol %, preferably about 1 to about 35 mol %; and $H_2$ from about 1 to about 98 mol %, preferably about 10 to about 90 mol %. The hydrogen should, however, be present in an amount which is in a molar excess over the amount of the carbon monoxide.

The residence time in the reactor may be, for example, as short as 10 or 20 seconds; or it may be, for example, as long as up to 4 hours. If a plurality of reactors is employed, the residence time may be, for example, as short as 10 to 15 seconds. Otherwise a preferred residence time is in the range of from about 30 seconds to about 5 minutes.

The preferred hydroformylation conditions that are employed convert substantially all the propylene during the hydroformylation reaction. We prefer to use rhodium catalysed hydroformylation at low pressures, because of the lower investment costs for the equipment, and the lower operating costs, for example for gas compression. However, it is desirable to keep up the hydrogen to carbon monoxide ratio during the hydroformylation reaction, and so it may be necessary to increase the hydrogen partial pressure; accordingly a higher overall pressure may be used. For targeting a higher selectivity to the n-butyraldehyde as compared to the isobutyraldehyde product from propylene hydroformylation, the partial pressure of CO in the reactor itself is preferably kept low, at least lower than the hydrogen partial pressure, but preferably lower than 0.5 MPaa, more preferably below 0.2 MPaa.

In a further embodiment of the invention the propylene feed stream that contains at least 97 mole % of propylene contains less than 500 ppb by weight of each of sulphur, nitrogen and chlorine, on an atomic weight basis. In a yet further embodiment the stream may contain more than 100 ppb by weight of dimethyl ether. The balance of the stream is generally primarily propane. Preferably, the stream contains less than 200 ppb, more preferably less than 150 ppb, most preferably less than 100 ppb, and particularly preferably less than 50 ppb, by weight, of each of sulphur, nitrogen and chlorine. In a much preferred embodiment, the propylene stream contains an aggregate total of sulphur, nitrogen and chlorine combined, on an atomic weight basis, of less than 100 ppb, more preferably less than 20 ppb, and most preferably less than 5 ppb.

The sulphur content of the propylene feed used in this invention, particularly as mercaptans but especially as carbonyl sulphide, is desirably sufficiently low that the activity of the catalyst used to form the hydroformylated product is not substantially inhibited. Ideally, the sulphur content in the propylene feed is not greater than about 1 ppm by weight on an atomic basis; progressively more preferably not greater than about 500 ppb, not greater than about 100 ppb, not greater than about 50 ppb, not greater than about 20 ppb, not greater than about 10 ppb, not greater than about 5 ppb, and most preferably, not greater than about 2 ppb by weight, calculated on an atomic basis.

The reactive nitrogen content of the propylene feed used in this invention, excluding $N_2$ but including reactive species like ammonia and amines, and particularly such highly reactive species like nitriles or other cyano compounds, are also desirably sufficiently low that the catalytic activity of the catalyst used to form the hydroformylated product is not substantially inhibited. Preferably, the active nitrogen content in the propylene feed is not greater than about 10 ppm; more preferably, not greater than about 5 ppm; and most preferably, not greater than about 2 ppm by weight, calculated on an atomic basis. More preferably, the active nitrogen content of the stream is not greater than about 1 ppm by weight on an atomic basis; progressively more preferably not greater than about 500 ppb, not greater than about 100 ppb, not greater than about 50 ppb, not greater than about 20 ppb, not greater than about 10 ppb, not greater than about 5 ppb, and most preferably, not greater than about 2 ppb by weight, calculated on an atomic basis. Ammonia itself may not have such a large effect on the catalytic activity of the catalyst, and may be tolerated in significantly higher amounts than nitriles or cyano compounds.

The chlorine content of the propylene feed used in this invention, in particular the ionic chlorine, is also desirably sufficiently low that the catalytic activity of the catalyst used to form the hydroformylated product is not substantially inhibited. Preferably, the chlorine content in the olefin feed is not greater than about 5 ppm; more preferably, not greater than about 2 ppm; and most preferably, not greater than about 1 ppm by weight, calculated on an atomic basis. More preferably, the ionic chlorine content of the stream is not greater than about 1 ppm by weight on an atomic basis; progressively more preferably not greater than about 500 ppb, not greater than about 100 ppb, not greater than about 50 ppb, not greater than about 20 ppb, not greater than about 10 ppb, not greater than about 5 ppb, and most preferably, not greater than about 2 ppb by weight, calculated on an atomic basis. Alkyl chlorides may not have such a large effect on the catalytic activity of the catalyst, and may be tolerated in significantly higher amounts than ionic chlorine.

We have found that the propylene containing stream used as feed according to the invention may contain a non-toxic amount of dimethyl ether. This means that dimethyl ether may be present in the stream delivered to the reactor, which provides the advantage that feed treatment for dimethyl ether removal is not necessary. However, excessive quantities are not desirable from the practical standpoint that in such cases, reactor volume is inefficiently utilized. A propylene stream containing for example up to about 5000 ppm by weight is highly acceptable. The lower the quantity of dimethyl ether, the greater the desirability from a hydroformylation operation standpoint. Feeds containing dimethyl ether at levels of up to about 4000 ppm by weight, up to about 3000 ppm by weight, up to about 2000 ppm by weight, up to about 1000 ppm by weight, up to about 500 ppm by weight or up to about 250 ppm by weight, may be used according to the invention.

We have found that the rhodium hydroformylation catalysts which are used in this invention are tolerant to the presence of such amounts of dimethyl ether. Suitable rhodium catalysts or catalyst precursors which can be used in this invention include rhodium(II) and rhodium(III) salts such as rhodium(III) chloride, rhodium(III) nitrate, rhodium(III) sulphate, potassium rhodium sulphate (rhodium alum), rhodium (II) or rhodium(III) carboxylate, preferably rhodium(II) and rhodium(III) acetate, rhodium(III) oxide, salts of rhodic(III) acid, triammonium hexachlororhodate (III).

In one embodiment of the invention, hydroformylation is carried out using an oil-soluble rhodium complex comprising a low valence rhodium (Rh) complexed both with carbon monoxide and a triorganophosphorus compound. The triorganophosphorus compound can include one or more oil-soluble triarylphosphines, tri alkylphosphines, alkyl-diarylphosphines, aryl-dialkylphosphines, triorganophosphites, particularly trialkylphosphites and triarylphosphites (in which list alkyl includes cycloalkyl), containing one or more phosphorus atoms per molecule capable of complexing with Rh by virtue of having a lone pair of electrons on the phosphorus.

In another embodiment, triorganophosphorus ligands can be used which preferably have (a) a molar P:Rh ratio of at least about 2:1, (b) a total concentration of phosphorus of at least about 0.01 mol/l; and (c) a [P]/Pco ratio maintained in the reactor of at least about 0.1 mmol/l/kPa, where [P] is the total concentration of the phosphorus in solution, expressed in mmol per liter, and Pco is the partial pressure of carbon monoxide in the gas phase, expressed in kPa. Examples of triorganophosphorus ligands include trioctylphosphine, tricyclohexylphosphine, octyldiphenylphosphine, cyclohexyldiphenylphosphine, phenyldioctylphosphine, phenyldicyclohexylphosphine, triphenylphosphine, tri-p-tolylphosphine, trinaphthylphosphine, phenyl-dinaphthylphosphine, diphenylnaphthylphosphine, tri-(p-methoxyphenyl)phosphine, tri-(p-cyanophenyl)phosphine, tri-(p-nitrophenyl)phosphine, and p-N,N-dimethylaminophenyl(diphenyl)phosphine, trioctylphosphite or tri-p-tolylphosphite. An example of a bidentate compound which can be used is diphos-bis(diphenylphosphino)ethane.

Preferably, Rh concentration in the reaction mixture is in a range of from about $1\times10^{-5}$ to about $1\times10^{-2}$ moles/liter or, in effect, in a range of from about 1 to about 1000 ppm or about 10 to 1000 ppm, preferably about 20 to about 500 ppm, more preferably from 25 to 350 ppm of rhodium, based on the total weight of the solution present in the reactor.

Organophosphite ligands can also be used for example those disclosed in U.S. Pat. Nos. 4,599,206, 4,668,651, 4,737,588, 4,748,261, 4,769,498, 4,774,361, 4,789,753, 4,835,299, 4,871,880, 4,885,401, 5,179,055, 5,288,918, 5,312,996, 5,364,950, 5,681,473, 5,756,855 and WO 97/20793. Preferred is 6,6'-[[3,3',5,5'-tetrakis(1,1-dimethylethyl)-1,1'-biphenyl-2,2'-diyl]bis(oxy)]bis-dibenzo[d,f][1,3,2]-dioxaphosphepin, or 6,6'-[[3,3',5,5'-tetrakis(1,1-dimethylpropyl)-1,1'-biphenyl-2,2'-diyl]bis(oxy)]bis-dibenzo[d,f][1,3,2]-dioxaphosphepin, or 6,6'-[[3,3'-bis(1,1-dimethylethyl)-5,5'-dimethoxy[1,1'-biphenyl]-2,2'-diyl]bis(oxy)]bis-dibenzo[d,f][1,3,2]-dioxaphosphepin, or tris(2,4,6-di-t-butylphenyl)-phosphite. Most preferred is 6,6'-[[3,3',5,5'-tetrakis(1,1-dimethylethyl)-1,1'-biphenyl-2,2'-diyl]bis(oxy)]bis-dibenzo[d,f][1,3,2]-dioxaphosphepin. Ionic varieties of such phosphites are disclosed in U.S. Pat. Nos. 5,059,710 and 5,113,022.

More recently bisphosphite ligands, e.g. of the formula

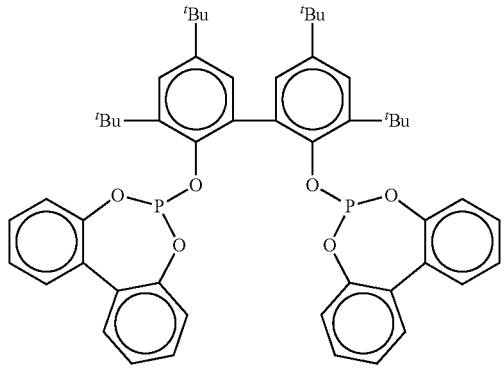

have been developed and these are described in U.S. Pat. Nos. 5,364,950, 4,835,299 and 5,288,918.

The hydroformylation process may generally be carried out in a manner known by persons skilled in the art, for example by the process according to U.S. Pat. Nos. 4,247,486, 4,287,370, 5,053,551, 6,100,432, WO 02/00582 or DE 10128325 although higher temperatures and/or carbon monoxide partial pressures may be used.

The catalyst is desirably contacted with the propylene feed stream in solution. The solution can comprise an oily solvent or a mixture of such solvents.

For example, aliphatic and aromatic hydrocarbons (e.g., heptanes, cyclohexane, toluene), esters (e.g., dioctyl phthalate), ethers, and polyethers (e.g., tetrahydrofuran, and tetraglyme), aldehydes (e.g., propanal, butanal) the condensation products of the oxo product aldehydes or the triorganophosphorus ligand itself (e.g., triphenylphosphine).

Alternatively, as described in U.S. Pat. Nos. 4,248,802, 4,808,756, 5,312,951 and 5,347,045, the catalyst may contain a hydrophilic group. In such a case, an aqueous medium may be used.

Rhodium can be introduced into the reactor as a preformed catalyst, for example, a solution of hydridocarbonyl tris (triphenylphosphine)rhodium(I); or it can be formed in situ. If the catalyst is formed in situ, the Rh may be introduced as a precursor such as acetylacetonatodicarbonyl rhodium(I) {Rh(CO)$_2$(acac)}, rhodium oxide {Rh$_2$O$_3$}, rhodium carbonyls {Rh$_4$(CO)$_{12}$, Rh$_6$(CO)$_{16}$}, tris(acetylacetonato)rhodium(I), {Rh(acac)$_3$}, or a triaryl phosphine-substituted rhodium carbonyl {Rh(CO)$_2$(PAr$_3$)}$_2$, wherein Ar is an aryl group.

During the hydroformylation reaction it is believed that the carbon monoxide competes with the phosphorus compound to co-ordinate as ligands to the rhodium metal. Accordingly a higher carbon monoxide partial pressure will co-ordinate more carbon monoxide with the rhodium and less of the much more bulky phosphorus containing ligand will co-ordinate. In this way the metal in the complex becomes more accessible for olefin bonds. Accordingly by increasing the partial pressure of the carbon monoxide, hydroformylation rates can be increased, especially with the bis-phosphite ligand system, but expectedly also with the older rhodium/triphenyl phosphine catalyst system. An additional affect of the higher partial pressures of carbon monoxide is a higher resistance of the rhodium complex against the formation of rhodium clusters, which become less and less active hydroformylation catalysts as more rhodium atoms tie up together, and ultimately may come out of solution and form precipitates. As this deactivation process goes faster at higher temperatures, the higher partial pressures of carbon monoxide permit the operation of the process at higher temperatures, and hence bring even higher additional benefits in terms of reaction rate, which can be translated into productivity, yield and/or investment benefits, or a combination thereof, as the practitioner may like. On the other hand, a higher carbon monoxide partial pressure may also favor the addition of the carbon monoxide to the non-terminal carbon on the olefinic bond, and hence e.g. favor the formation of isobutyraldehyde at the expense of n-butyraldehyde. When the normal butyraldehyde is the more preferred isomer, a lower carbon monoxide partial pressure may therefore be preferred.

As an extension of the process of the invention the n-butyraldehyde produced by the hydroformulation process of this invention may then be converted to 2 ethyl hexanol or mixtures containing 2-ethyl-hexanol by dimerisation, usually by an aldol reaction, and suitably followed by hydrogenation. The aldolisation may be carried out in the presence of some isobutyraldehyde, so that the 2-ethyl hexanol produced may also contain some 2-ethyl-4-methyl-pentanol. The hydrogenation may be selective to saturate only the alkyl chain and not the aldehyde functionality, such that a saturated aldehyde is formed. Such aldehyde, or mixtures of aldehydes, are readily oxidised to the corresponding acid, such as 2-ethyl hexanoic acid. Alternatively, the n-butyraldehyde and/or isobutyraldehyde, or a mixture thereof, may be hydrogenated to their respective alcohols or a mixture thereof, or they may be oxidised to the corresponding acids, or a mixture thereof.

Such acids and alcohols may be further reacted to commercially interesting derivatives. Acid derivatives include polyol esters and metal salts. Alcohol derivatives also include esters such as phthalates, adipates, acetates, nitrates, acrylates, sulfates and phosphates, but also other surfactant derivatives such as alkoxylates and alkoxysulfates.

According to one embodiment of the invention, therefore, hydroformylation may be accomplished using phosphite ligands with careful control of the temperatures and partial pressures of the reactants and/or products. Thus, when a triorganophosphine ligand is used it is preferably used in an amount of at least 100 mole per gram atom of rhodium. Contrarily, if one prefers to forego the high selectivity to the normal aldehyde, one may use amounts of triorganosphosphine ligand that are much lower, like 40 or less mole per gram atom of rhodium, but also 20 or less, and even 10 or less, down to 5 or less, or even 2 or less, should one desire to do so. Preferably with bis-phosphite ligands the amount of ligand present is from 1 to about 40 moles of bisphosphite ligand per mole of rhodium, more preferably from 1 to 8 moles ligand per mole rhodium, and most preferably from 1 to 4 moles of bisphosphite ligand per mole of rhodium, said amount of ligand being the sum of both the amount of ligand that is bound (complexed) to the rhodium metal and the amount of free (non-complexed) ligand present. If desired, make-up ligand can be supplied to the reaction medium of the process at any time and in any suitable manner, e.g. to maintain a predetermined level of free ligand in the reaction medium.

In general $H_2$ to CO molar ratio of gaseous hydrogen to carbon monoxide is >1:1. Thus the ratio may, for example, range from about >1:1 to 100:1 or higher. The more preferred hydrogen to carbon monoxide molar ratio is from about >1:1 to about 10:1, most preferably from 1.1:1 to 1.2:1. Further, the hydroformylation process may be conducted at a reaction temperature from about 45° C. to about 180° C. In general hydroformylation reaction temperatures of about 50° C. to about 170° C. are preferred, the more preferred reaction temperatures being from about 80° C. to about 160° C. and most preferably from about 90, 100, 110, 120, 130 or 140° C. upwards.

Since the hydroformylation process of the invention advantageously takes place in the liquid phase and the reactants are gaseous compounds, a high contact surface area between the gas and liquid phases is desirable to avoid mass transfer limitations. A high contact surface area between the catalyst solution and the gas phase can be obtained in a variety of ways. For example, the olefin feed stream can be contacted with catalyst solution in, for example, a continuous-flow stirred reactor where the feed is introduced and dispersed at the bottom of the vessel, preferably through a perforated inlet. Good contact between the catalyst and the gas feed can also be ensured by dispersing a solution of the catalyst on a high surface area support. Such a technique is commonly referred to as supported liquid phase catalysis. The catalyst can also be provided as part of a permeable gel.

The hydroformylation reaction can be performed in a single reactor. Examples of suitable reactors can be found in U.S. Pat. Nos. 4,287,369; 4,287,370; 4,322,564; 4,479,012 and EP-A-114,611; EP-A-103,810 and EP-A-144,745. Two or more reactor vessels or reactor schemes configured in parallel or in series can also be used. In addition, a plug flow reactor design, optionally with partial liquid product backmixing, can give an efficient use of reactor volume. It is preferred that the hydroformylation reaction be carried out in more than one reaction zone or vessel in series. Suitable reactor configurations are disclosed, for example, by British Patent 1,387,657 and U.S. Pat. Nos. 4,593,127; 5,105,018 and 5,367,106. Examples of individual hydroformylation reactors can of the standard types described by Denbigh and Turner in "Chemical Reactor Theory" ISBN 0 521 07971 3, by Perry et al in "Chemical Engineers' Handbook" ISBN 0-07-085547-1 or any more recent editions, e.g., a continuous stirred tank or a plug flow reactor with adequate contact of the gas and the liquid flowing through the reactor. Advantageously these plug flow reactor designs or configurations include ways of partial backmixing of the reactor product liquid, as explained, for example in DE 3,220,858.

By using the conditions of the present invention we have found that the efficiency of industrial scale propylene hydroformylation may be improved to a surprising extent. Thus, by increasing the propylene content of the feed to the mole % required by the inventor, it is possible, within the contraints of a plant's gas recycle capability, to increase the amount of hydroformylation product produced for a fixed amount of feed to the reactor. Rather than keeping the feed constant, it is possible to maintain the capacity of the plant with a reduction in feed throughput. Of course optimum commercial operation may involve a combination of these two (capacity or efficiency) advantages. We have found for example that, providing these conditions of the invention are employed, an increase in the propylene content of the feed from 95 to at least 97.5 mole % results in an increase in capacity of a nominal 100,000 tonne per year facility to 103200 tonnes per year. An increase in the propylene content from 95 mole % to 99.5% results in an increase in capacity to 105800 tonnes per year. We have also found that the utilisation of syngas is improved and that the energy efficiency of the plant, particularly the power required for the compressor systems, is reduced. Waste due to by product venting is also considerably reduced.

Accordingly for a given hydroformylation reactor size and for a given recycle gas compressor capacity and maintaining the concentration and stability of the catalyst, we have found that by increasing the propylene content of the feed from 95 mole % to 99.5 mole % it is possible within the same reactor equipment and recycle compressor volumetric flow limitations, to produce 5.8% more butyraldehyde, and this is achievable at only 94.0% of the propylene containing feed stream flow, per unit of butyraldehyde product, compared with the 95 mole % propylene in feed case. Furthermore the requirements for gas disposal may be reduced by about 35% by weight. If the propylene content of the feed is 97.5 mole % instead of 95 mole %, butyraldehyde production may be increased by 3.2%. Again, this is achievable at only 96.6% of the propylene containing feedstream flow. Gas venting requirements may be reduced to 80.2% of the original case.

EXAMPLES

Example 1

The improvements in efficiency in the production of butyraldehyde are shown in the following Table 1 which compares the material balances for the hydroformylation of chemical grade propylene (containing 95.0 mole % propylene); and polymer grade propylene (containing 99.5 mole % propylene). The material balances are shown for a hydroformylation conducted by the process illustrated in FIG. 1, which shows a simplified flow scheme of a butyraldehyde process using low pressure rhodium hydroformylation technology. Propylene feed (1) and syngas feed (2) are mixed with gas recycle stream (5) and fed to the hydroformylation (LPO) reactor (100). Leaving the overhead entrainment separator (101) is reactor effluent (4), which after cooling in condensor (102) is separated into gas and liquid in separator (103). The gas from this separator is partially purged as vent gas (6), and the remainder is recycled via first compressor (104). The liquid from separator (103) is fed via line (7) to a stabiliser (105), although some may be returned via line 10 to the LPO reactor (100). In stabiliser (105), light components are removed as stabiliser overhead gas (9), which is recycled by second compressor (106) to the gas recycle loop that is driven by the first compressor (104). Most of the butyraldehyde product leaves with the stabiliser bottom stream (8). Although the invention is also advantageous in other possible low pressure rhodium hydroformylation flow schemes known in the art, it is particularly advantageous for the process illustrated in FIG. 1.

The catalyst solution contained 27 wtppm rhodium.

The catalyst solution was transferred into the reactor and the reactor was purged several times with syngas to remove air. The reactor content was then heated up to 110° C. under 200 kPag (2 barg) syngas pressure. Once the desired reaction temperature was reached, about 0.05 mol propylene was injected into the catalyst solution by means of synthesis gas and at the same time as the injection of propylene the pressure was adjusted to 1000 kPag (10 barg).

Immediately after the substrate injection and pressure adjustment, the progress of the reaction was followed by measuring the rate of gas consumption, indicated by the pressure decay (DELTA-P) in the high pressure syngas storage cylinder.

The reaction was run for 3 hours and at the end of the reaction the gas supply was stopped and the reactor was cooled down to room temperature. A gas sample was taken from the gas phase inside the reactor and analysed on a HP6890 gas chromatograph (supplied by Hewlett-Packard). The chromatograph was equipped with a thermal conductiv-

TABLE 1

Calculated Plant Material Balance

| Propylene feed quality | | Chemical Grade (CG) | Polymer Grade | Relative to CG | Comments |
|---|---|---|---|---|---|
| Propylene content | Mole % | 95.0 | 99.5 | | Balance is primarily propane |
| Propylene feed (1) flow | kg/h | 10000 | 9947 | 99.5% | |
| Contained propylene | kg/h | 9477 | 9895 | 105.6% | |
| Syngas feed (2) flow | kg/h | 6460 | 6825 | 105.6% | $H_2/CO = 1.18$; and methane + $CO_2$ = 2.0 mole % |
| ($H_2$ + CO)/ propylene mole ratio | — | 1.9219 | 1.9448 | 101.2% | |
| Propylene converted | kg/h | 8841 | 9357 | 105.8% | |
| Butyraldehyde (n + iso) production rate | | | | | |
| As recovered [in (8)] | kg/h | 14634 | 9357 | 105.8% | Capacity gain |
| Vent gas by product (6) flow | kg/h | 1751 | 1205 | 63.8% | Downgraded to fuel gas |
| Product utilization (flows per unit of butyraldehyde recovered) | | | | | |
| Propylene feed (1) | kg/kg | 0.683 | 0.642 | 94.0% | Efficiency gain |
| Syngas feed (2) | kg/kg | 0.491 | 0.441 | 99.82% | |
| Total feeds (1 + 2) | kg/kg | 1.125 | 1.083 | 96.3% | Efficiency gain |
| Vent gas by-product (6) | kg/kg | 0.120 | 0.078 | 65.0% | Efficiency gain |

Example 2

It has been projected that the following findings will translate to the conditions of the present invention including a continuous process in which the propylene feed is delivered at a rate of at least 3 tonnes per hour. Hydroformylation kinetic experiments were carried out in a standard half liter zipperclave from Autoclave Engineers. Mixing occurred with an air driven stirrer with speed controlled at 2000 revolutions per minute. The mixer had a six bladed impeller that guaranteed a strong mixing between the gas and the liquid phase. Baffles inside the reactor prevented vortex formation and created back mixing. The reaction temperature was controlled at 110° C.+/−1° C. Pressure was controlled at 1000 kPag±10 kPa (10 barg+/−0.1 bar). Synthesis gas (48% $H_2$ and 52% CO) was delivered from a calibrated high pressure storage cylinder equipped with a pressure transmitter allowing pressure reading at 1 kPa (0.01 bar) accuracy. Each experiment started with a catalyst solution of the following composition:

Triphenyl phosphine (TPP)=19.84 g
Tetraglyme (solvent)=191.2 g
Rhodium=0.00576 g The rhodium was dosed using rhodium carbonyl acetylacetonate as catalyst precursor.

ity detector (TDC) detection system and a poraplotQ column of 30 m length, 0.53 mm internal diameter (ID), 10 μm df (standing for "dense phase", and indicating film thickness). A liquid sample was withdrawn from the reactor into a cooled sample vial and analysed for product composition by gas chromatography using a HP6890 gas chromatograph equipped with a Flame Ionisation Detector (FID) detection system and a wall coated open tubular (WCOT) Ultimetal column of 10 m length, 0.53 mm ID, 0.17 μm df. The column (HT Simdist CB) is a chemically bound high temperature simulated distillation column. "Ultimetal" and "poraplotQ" are trade names of the Varian-Chrompack company.

Sulphur analyses of the products were performed on a HP6890 gas chromatograph equipped with a fused silica column and a model 355 flameless sulphur chemoluminescence detector from Sievers. The column was a CPSIL5CB chemically bound silica column supplied by Chrompack of 30 m length, 0.32 mm ID, and 5 μm df. This method gives quantitative information both about total sulphur and about individual sulphur components in the product with a detection limit of about 5 wtppb.

Finally the reactor was depressurised and the liquid recovered and weighed. From the weight of the product, its composition and the composition of the off-gas the end-conversion was calculated. The conversion at any given moment could then be calculated pro-rata the pressure drop at that moment, the measured end-conversion and the total pressure drop achieved at the end of the experiment.

Two experiments served as reference case, providing a base case reaction rate for propylene hydroformylation with rhodium and triphenyl phosphine in absence of any impurity. The two runs also served to demonstrate the reproducibility of the experiments and the results of these experiments are shown in Tables 2 and 3 (and FIGS. 2 and 3). In those Tables, TPP stands for triphenylphosphine; TPPO stands for triphenylphosphine oxide; and TEGDE stands for tetra-ethylene glycol dimethyl ether (also known as tetraglyme).

Figure 4:
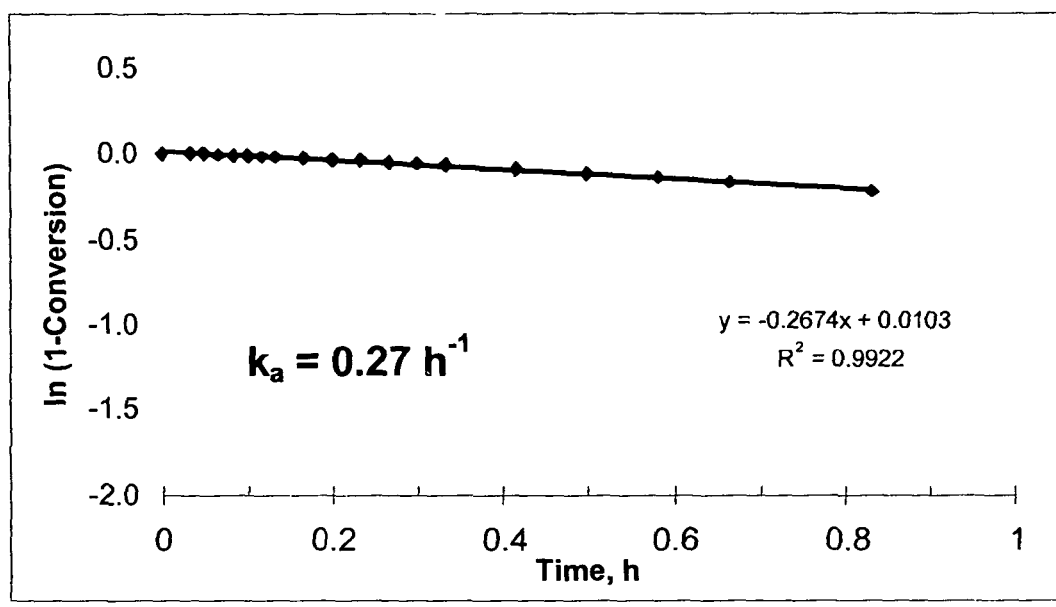

In the run reported in Table 4 and FIG. 4, 0.0011 moles of methyl mercaptan were added and Table 4 and FIG. 4 illustrates that sulphur is a catalyst poison for the rhodium hydroformylation and significantly reduces the reaction rate.

Figure 2:
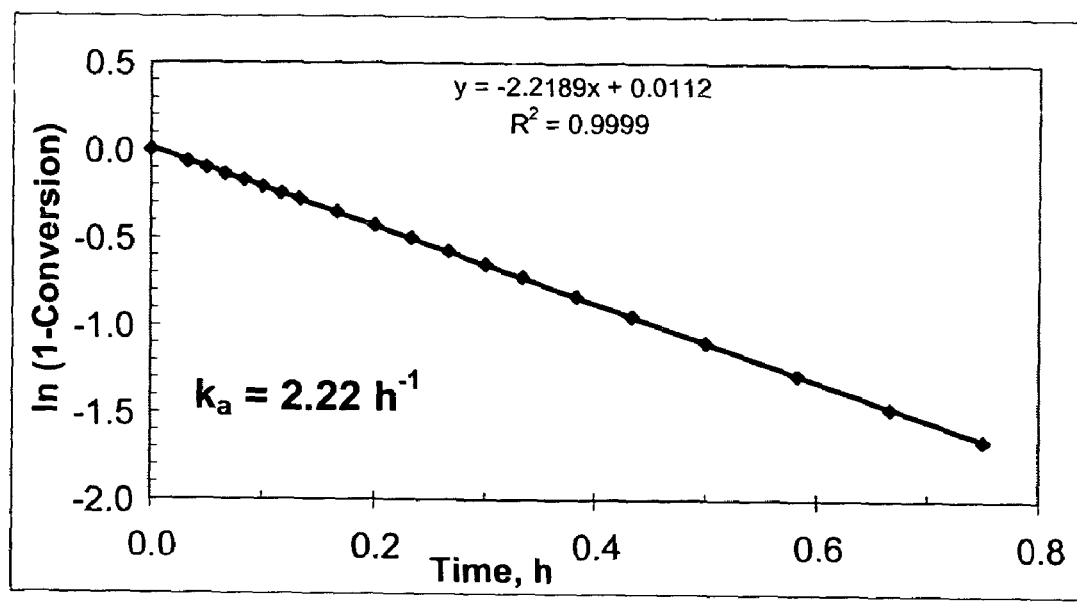
FIGS. 2-4 are graphs of the conversion data of Tables 2-4.
Figure 3:
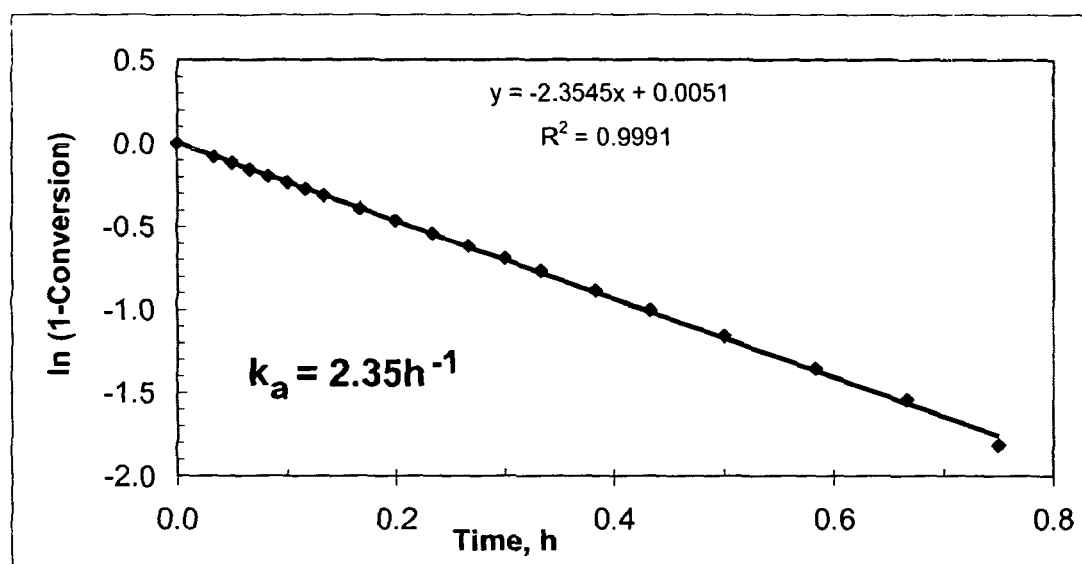

At 110° C., the graphs of ln(1−conversion) versus time in FIGS. 2 and 3 showed a linear slope for about the first hour, and first order initial reaction rates of 2.22 $h^{-1}$ and 2.35 $h^{-1}$ were measured respectively for the two reference runs.

TABLE 2

Propylene reference run 1

| PRODUCT COMPOSITION | Wt % | g | moles |
|---|---|---|---|
| Propylene | 0.01 | 0.02 | 0.0005 |
| i-butanal | 0.48 | 1.00 | 0.0139 |
| n-butanal | 1.85 | 3.86 | 0.0536 |
| TPP | 9.43 | 19.70 | 0.0751 |
| TPPO | 0.48 | 1.00 | 0.0036 |
| Butyric acid | 0.03 | 0.06 | 0.0007 |
| TEGDE | 87.71 | 183.23 | 0.8243 |
| C3 in off gas | | 0.0110 | 0.0003 |
| Substrate conversion | | 98.80% molar | |

| time, min | DELTA P | Conversion | 1-conversion | ln(1-conv) |
|---|---|---|---|---|
| 0 | 0.000 | 0.000 | 1.000 | 0.000 |
| 2 | 0.860 | 6.561 | 0.934 | −0.068 |
| 3 | 1.290 | 9.842 | 0.902 | −0.104 |
| 4 | 1.690 | 12.893 | 0.871 | −0.138 |
| 5 | 2.090 | 15.945 | 0.841 | −0.174 |
| 6 | 2.490 | 18.996 | 0.810 | −0.211 |
| 7 | 2.860 | 21.819 | 0.782 | −0.246 |
| 8 | 3.210 | 24.489 | 0.755 | −0.281 |
| 10 | 3.930 | 29.982 | 0.700 | −0.356 |
| 12 | 4.580 | 34.941 | 0.651 | −0.430 |
| 14 | 5.180 | 39.519 | 0.605 | −0.503 |
| 16 | 5.740 | 43.791 | 0.562 | −0.576 |
| 18 | 6.270 | 47.834 | 0.522 | −0.651 |
| 20 | 6.750 | 51.496 | 0.485 | −0.724 |
| 23 | 7.420 | 56.608 | 0.434 | −0.835 |
| 26 | 8.030 | 61.262 | 0.387 | −0.948 |
| 30 | 8.730 | 66.602 | 0.334 | −1.097 |
| 35 | 9.480 | 72.324 | 0.277 | −1.285 |
| 40 | 10.110 | 77.130 | 0.229 | −1.475 |
| 45 | 10.610 | 80.945 | 0.191 | −1.658 |
| 50 | 11.060 | 84.378 | 0.156 | −1.856 |
| 55 | 11.410 | 87.048 | 0.130 | −2.044 |
| 60 | 11.690 | 89.184 | 0.108 | −2.224 |
| 90 | 12.530 | 95.592 | 0.044 | −3.122 |
| 120 | 12.830 | 97.881 | 0.021 | −3.854 |
| 180 | 12.950 | 98.797 | 0.012 | −4.420 |

TABLE 3

Propylene reference run 2

| PRODUCT COMPOSITION | Wt % | g | moles |
|---|---|---|---|
| Propylene | 0.01 | 0.02 | 0.0005 |
| i-butanal | 0.43 | 0.90 | 0.0125 |
| n-butanal | 1.67 | 3.49 | 0.0484 |
| TPP | 9.27 | 19.39 | 0.0740 |
| TPPO | 0.55 | 1.15 | 0.0041 |
| Butyric acid | 0.04 | 0.08 | 0.0009 |
| TEGDE | 88.03 | 184.16 | 0.8285 |
| C3 in off gas | | 0.0083 | 0.0002 |
| Substrate conversion | | 98.61% molar | |

| time, min | DELTA P | Conversion | 1-conversion | ln(1-conv) |
|---|---|---|---|---|
| 0 | 0.000 | 0.000 | 1.000 | 0.000 |
| 2 | 0.890 | 7.732 | 0.923 | −0.080 |
| 3 | 1.300 | 11.294 | 0.887 | −0.120 |
| 4 | 1.680 | 14.596 | 0.854 | −0.158 |
| 5 | 2.050 | 17.810 | 0.822 | −0.196 |
| 6 | 2.400 | 20.851 | 0.791 | −0.234 |
| 7 | 2.750 | 23.892 | 0.761 | −0.273 |
| 8 | 3.090 | 26.846 | 0.732 | −0.313 |
| 10 | 3.700 | 32.146 | 0.679 | −0.388 |
| 12 | 4.280 | 37.185 | 0.628 | −0.465 |
| 14 | 4.800 | 41.702 | 0.583 | −0.540 |
| 16 | 5.300 | 46.046 | 0.540 | −0.617 |
| 18 | 5.750 | 49.956 | 0.500 | −0.692 |
| 20 | 6.170 | 53.605 | 0.464 | −0.768 |
| 23 | 6.770 | 58.818 | 0.412 | −0.887 |
| 26 | 7.290 | 63.335 | 0.367 | −1.003 |
| 30 | 7.900 | 68.635 | 0.314 | −1.159 |
| 35 | 8.550 | 74.282 | 0.257 | −1.358 |
| 40 | 9.050 | 78.626 | 0.214 | −1.543 |
| 45 | 9.640 | 83.752 | 0.162 | −1.817 |
| 50 | 9.850 | 85.577 | 0.144 | −1.936 |
| 55 | 10.070 | 87.488 | 0.125 | −2.078 |
| 60 | 10.300 | 89.486 | 0.105 | −2.252 |
| 90 | 11.100 | 96.437 | 0.036 | −3.334 |
| 120 | 11.300 | 98.174 | 0.018 | −4.003 |
| 180 | 11.350 | 98.609 | 0.014 | −4.275 |

TABLE 4

Effect of methylmercaptan

| PRODUCT COMPOSITION | Wt % | g | moles |
|---|---|---|---|
| Propylene | 0.35 | 0.73 | 0.0174 |
| i-butanal | 0.38 | 0.80 | 0.0110 |
| n-butanal | 1.52 | 3.18 | 0.0441 |
| TPP | 9.82 | 20.55 | 0.0784 |
| TPPO | 0.16 | 0.33 | 0.0012 |
| Butyric acid | 0.03 | 0.06 | 0.0007 |
| TEGDE | 87.72 | 183.60 | 0.8260 |
| C3 in off gas | | 0.1700 | 0.0040 |
| Substrate conversion | | 57.02% molar | |
| Sulphur in product, wtppm | | 238 | |

| time, min | DELTA P | Conversion | 1-conversion | ln(1-conv) |
|---|---|---|---|---|
| 0 | 0.000 | 0.000 | 1.000 | 0.000 |
| 2 | 0.090 | 0.524 | 0.995 | −0.005 |
| 3 | 0.120 | 0.699 | 0.993 | −0.007 |
| 4 | 0.170 | 0.990 | 0.990 | −0.010 |
| 5 | 0.220 | 1.281 | 0.987 | −0.013 |
| 6 | 0.270 | 1.573 | 0.984 | −0.016 |
| 7 | 0.370 | 2.155 | 0.978 | −0.022 |
| 8 | 0.430 | 2.505 | 0.975 | −0.025 |
| 10 | 0.550 | 3.203 | 0.968 | −0.033 |
| 12 | 0.670 | 3.902 | 0.961 | −0.040 |
| 14 | 0.780 | 4.543 | 0.955 | −0.046 |
| 16 | 0.940 | 5.475 | 0.945 | −0.056 |
| 18 | 1.060 | 6.174 | 0.938 | −0.064 |
| 20 | 1.130 | 6.582 | 0.934 | −0.068 |
| 25 | 1.580 | 9.203 | 0.908 | −0.097 |

TABLE 4-continued

Effect of methylmercaptan

| | | | | |
|---|---|---|---|---|
| 30 | 1.970 | 11.474 | 0.885 | −0.122 |
| 35 | 2.320 | 13.513 | 0.865 | −0.145 |
| 40 | 2.680 | 15.610 | 0.844 | −0.170 |
| 50 | 3.450 | 20.094 | 0.799 | −0.224 |
| 60 | 3.810 | 22.191 | 0.778 | −0.251 |
| 90 | 5.240 | 30.520 | 0.695 | −0.364 |
| 120 | 6.840 | 39.839 | 0.602 | −0.508 |
| 180 | 9.790 | 57.021 | 0.430 | −0.844 |

The invention claimed is:

1. A continuous process for the hydroformylation of propylene comprising feeding
   (i) a propylene stream at a rate of at least 3 tonnes per hour, and
   (ii) synthesis gas comprising hydrogen and carbon monoxide to a hydroformylation reactor wherein the propylene is hydroformylated over a rhodium containing catalyst, and wherein
      (a) the propylene stream contains at least 97 mole % of propylene;
      (b) the molar ratio of ($H_2$+CO) contained in the fresh synthesis gas fed to the reactor, to the propylene contained in the fresh propylene stream fed to the reactor, is greater than 1.93; and
      (c) in the synthesis gas feed, the hydrogen over carbon monoxide molar ratio is from >1:1 to 1.2:1 and thereby by producing a hydroformylated product comprising butyraldehyde.

2. The process according to claim 1 wherein the propylene stream contains at least 99.5 mole % of propylene.

3. The process according to claim 1 wherein the sulphur content of the propylene feed is not greater than 500 ppb by weight, calculated on an atomic basis.

4. The process according to claim 3 wherein the reactive nitrogen content of the propylene feed is not greater than 10 ppm by weight, calculated on an atomic basis.

5. The process according to claim 4 wherein the chlorine content of the propylene feed is not greater than 5 ppm by weight, calculated on an atomic basis.

6. The process according to claim 5 wherein the chlorine content of the propylene feed is not greater than 50 ppb by weight, calculated on an atomic basis.

7. The process according to claim 4 wherein the reactive nitrogen content of the propylene feed is not greater than 50 ppb by weight, calculated on an atomic basis.

8. The process according to claim 7 wherein the chlorine content of the propylene feed is not greater than 5 ppm by weight, calculated on an atomic basis.

9. The process according to claim 8 wherein the chlorine content of the propylene feed is not greater than 50 ppb by weight, calculated on an atomic basis.

10. The process according to claim 3 wherein the chlorine content of the propylene feed is not greater than 5 ppm by weight, calculated on an atomic basis.

11. The process according to claim 10 wherein the chlorine content of the propylene feed is not greater than 50 ppb by weight, calculated on an atomic basis.

12. The process according to claim 3 wherein the sulphur content of the propylene feed is not greater than 50 ppb by weight, calculated on an atomic basis.

13. The process according to claim 12 wherein the reactive nitrogen content of the propylene feed is not greater than 10 ppm by weight, calculated on an atomic basis.

14. The process according to claim 13 wherein the chlorine content of the propylene feed is not greater than 5 ppm by weight, calculated on an atomic basis.

15. The process according to claim 14 wherein the chlorine content of the propylene feed is not greater than 50 ppb by weight, calculated on an atomic basis.

16. The process according to claim 13 wherein the reactive nitrogen content of the propylene feed is not greater than 50 ppb by weight, calculated on an atomic basis.

17. The process according to claim 16 wherein the chlorine content of the propylene feed is not greater than 5 ppm by weight, calculated on an atomic basis.

18. The process according to claim 17 wherein the chlorine content of the propylene feed is not greater than 50 ppb by weight, calculated on an atomic basis.

19. The process according to claim 12 wherein the chlorine content of the propylene feed is not greater than 5 ppm by weight, calculated on an atomic basis.

20. The process according to claim 19 wherein the chlorine content of the propylene feed is not greater than 50 ppb by weight, calculated on an atomic basis.

21. The process according to claim 1 wherein the reactive nitrogen content of the propylene feed is not greater than 10 ppm by weight, calculated on an atomic basis.

22. The process according to claim 21 wherein the chlorine content of the propylene feed is not greater than 5 ppm by weight, calculated on an atomic basis.

23. The process according to claim 22 wherein the chlorine content of the propylene feed is not greater than 50 ppb by weight, calculated on an atomic basis.

24. The process according to claim 21 wherein the reactive nitrogen content of the propylene feed is not greater than 50 ppb by weight, calculated on an atomic basis.

25. The process according to claim 24 wherein the chlorine content of the propylene feed is not greater than 5 ppm by weight, calculated on an atomic basis.

26. The process according to claim 25 wherein the chlorine content of the propylene feed is not greater than 50 ppb by weight, calculated on an atomic basis.

27. The process according to claim 1 wherein the chlorine content of the propylene feed is not greater than 5 ppm by weight, calculated on an atomic basis.

28. The process according to claim 27 wherein the chlorine content of the propylene feed is not greater than 50 ppb by weight, calculated on an atomic basis.

29. The process according to claim 18 wherein the aggregate weight content in the propylene feed of sulphur and reactive nitrogen and chlorine, on an atomic basis, is less than 50 ppb.

30. The process according to claim 1 wherein the hydroformylation catalyst is an oil-soluble rhodium complex comprising a low valence rhodium (Rh) complexed with a triorganophosphorus compound.

31. The process according to claim 30 wherein the triorganophosphorus compound is selected from the group consisting of an oil-soluble triarylphosphine, trialkylphosphine, alkyl-diaryl-phosphine, aryl-dialkylphosphine, triorganophosphite and bisphosphite containing, per molecule, at least one phosphorus atom capable of complexing with Rh.

32. The process according to claim 31 wherein the triorganophosphorus compound is triphenylphosphine or 6,6'-[[3,3',5,5'-tetrakis(1,1-dimethylethyl)-1,1'-biphenyl-2,2'-diyl]bis(oxy)]bis-dibenzo[d,f][1,3,2]-dioxaphosphepin.

33. The process according to claim 1 wherein the Rh concentration in the hydroformylation reaction mixture is in the range of from $1 \times 10^{-5}$ to $1 \times 10^{-2}$ moles/liter.

34. The process according to claim 1 wherein the hydroformylation is carried out at a temperature in the range of from 40 to 200° C.

35. The process according to claim 1 wherein the hydroformylation is carried out at a pressure in the range of from 0.05 to 10 MPaa.

36. The process according to claim 1 wherein the carbon monoxide partial pressure in the reactor is not greater than 50% of the total pressure.

37. The process according to claim 1 wherein the propylene feed stream contains up to 5000 ppb by weight of dimethyl ether.

38. The process according to claim 37 wherein the propylene feed stream contains, by weight and on an atomic basis, less than 50 ppb sulphur, less than 50 ppb reactive nitrogen and less than 50 ppb chlorine.

39. The process according to claim 38 wherein the aggregate weight content in the propylene feed of sulphur and reactive nitrogen and chlorine, on an atomic basis, is less than 50 ppb.

40. The process according to claim 1 wherein the molar ratio of ($H_2$+CO) to propylene is greater than 1.94.

41. The process according to claim 1 wherein the molar ratio of hydrogen to carbon monoxide is from 1.1:1 to 1.2:1.

42. The process according to claim 1 further comprising aldolising the hydroformylation product, followed by hydrogenating the aldolisation product to form an alcohol product selected from 2-ethyl-hexanol and mixtures containing 2-ethyl-hexanol.

43. The process according to claim 1 wherein a product of the process of claim 1 is a butyraldehyde, the process further comprising hydrogenating the butyraldehyde to the corresponding alcohol.

44. The process according to claim 1 wherein a product of the process of claim 1 is a butyraldehyde, the process further comprising oxidizing the butyraldehyde, to the corresponding acid.

* * * * *